United States Patent
Ospina Sánchez et al.

(10) Patent No.: US 8,642,296 B2
(45) Date of Patent: Feb. 4, 2014

(54) **BIOPOLYMER BASED ON *LACTOCOCCUS LACTIS* NRRL B-30656, PROCESS FOR CULTURING *LACTOCOCCUS LACTIS* NRRL B-30656, AND PREPARING THE BIOPOLYMER**

(75) Inventors: Sonia Amparo Ospina Sánchez, Bogota (CO); Dolly Montoya Castaño, Bogota (CO); Gustavo Buitrago Hurtado, Bogota (CO); Jairo Alonso Ceron Salamanca, Bogota (CO); Oscar Caicedo Zamora, Bogota (CO)

(73) Assignee: Universidad Nacional de Colombia, Bogata (CO)

( * ) Notice: Subject to any disclaimer, the term of this patent is extended or adjusted under 35 U.S.C. 154(b) by 1792 days.

(21) Appl. No.: 10/584,446

(22) PCT Filed: Dec. 21, 2004

(86) PCT No.: PCT/IB2004/004224
§ 371 (c)(1),
(2), (4) Date: Jan. 8, 2007

(87) PCT Pub. No.: WO2005/064003
PCT Pub. Date: Jul. 14, 2005

(65) Prior Publication Data
US 2007/0141667 A1 Jun. 21, 2007

(30) Foreign Application Priority Data

Dec. 23, 2003 (CO) .................................. 03112173

(51) Int. Cl.
*C12P 19/18* (2006.01)
(52) U.S. Cl.
USPC .......................................................... 435/97
(58) Field of Classification Search
USPC .......................................................... 435/97
See application file for complete search history.

(56) References Cited

FOREIGN PATENT DOCUMENTS

WO WO-01/57234 A2 8/2001

OTHER PUBLICATIONS

Maria C. Manaca De Nardra et al. "Polysaccharide production by *Pediococcus pentosaceus* from wine" International Journal of Food Microbiology 27 (1995) 101-106.*
De Vuyst, L.D. et al., International Dairy Journal 11, pp. 687-707 (2001).
Manca, M.C. et al., Extracellular polysaccharide production by *Lactobacillus bulgaricus* CRL 42. Milchwissenschaft, vol. 40, pp. 409-411 (1985).

* cited by examiner

*Primary Examiner* — Thane Underdahl
(74) *Attorney, Agent, or Firm* — Birch, Stewart, Kolasch & Birch, LLP

(57) ABSTRACT

A microorganism identified as a *Lactococcus lactis* strain (NRRL B-30656) produces an extracellular transferase enzyme when cultured and grown in sucrose-containing medium, which can be purified when it is brought into contact with a sucrose-based medium in suitable temperature and pH conditions, thereby producing a glucose and fructose polymer.

7 Claims, No Drawings

BIOPOLYMER BASED ON *LACTOCOCCUS LACTIS* NRRL B-30656, PROCESS FOR CULTURING *LACTOCOCCUS LACTIS* NRRL B-30656, AND PREPARING THE BIOPOLYMER

BACKGROUND OF THE INVENTION

1. Field of the Invention

This invention relates to a glucose and fructose polymer and the method for preparing it using a *Lactococcus lactis* strain. The exopolysaccharides are natural glucose and fructose polymers. These polymers can be found in several plants and microorganisms and are useful as emulsifiers, thickener and surfactants in the food and medicaments industries.

2. Description of the State of the Art

Fructosans naturally occur in two general forms differentiated by the type of binding between molecules of fructose: inulin, as found in plants, is formed from a column of fructose molecules bound by beta,2-1 links. Levans, formed as microbial products, have a column of fructose molecules bound by beta,2-6 links. The fructosans from plants are smaller (around 100 residues) whilst microbial levans contain more than 3 million residues (Pontis et al., 1985, Biochemistry of Storage Carbohydrates in Green Plants. In: Dey and Dixon (eds). Ch. 5, p. 205. New York, Academic Press).

Microbial Levans are produced with sucrose-based substrates having a variety of microorganisms: Acetobacters (Loewenberg, et al., 1957. Can. J. Microbiol., Vol. 3, p. 643), *Achromobacter* sp. (Lindberg, G., 1957. Nature. Vol. 180, p. 1141), *Aerobacter aerogenes* (Srinivasan, et al., 1958. Science. Vol. 127, p. 143), *Phytobacterium vitrosum* (Belval, et al., 1947. 1948. Compt. Rend. Vol. 224, p. 847 and Vol. 226, p. 1859), *Xanthomonas pruni* (Cooper, et al., 1935. Biochem. J. Vol. 29, p. 2267), *Bacillus subtilis* (Dedonder, R., 1966. Meth. Enzymol. Vol. 8, p. 500 and Tanka, et al., 1979. J. Biochem., Vol. 85, p. 287), *Bacillus polymyxa* (Hestrin et al., 1943. Biochem. J., Vol. 3, p. 450), *Aerobacter levanicum* (Hestrin, et al., Ibid.), *Streptococcus* sp. (Corrigen et al., 1979. Infect. Immun., Vol. 26, p. 387), *Pseudomonas* sp. (Fuchs, A., 1956. Nature. Vol. 178, p. 92) and *Corynebacterium laevaniformans* (Dias et al., 1962. Antonie Van Leewenhoeck, Vol. 28, p. 63).

There are some reports of levan being produced at very low levels and having low purity to be used industrially.

Other biological polymers such as xantan and dextran gum have been extensively used in the food industry as stabilisers in emulsions and froth in ice-cream, in salad-dressing, etc. (Sharma, S. C., January 1981. J. Food Tech., p. 59). Extracellular polysaccharides produced by microorganisms offer a variety of uses and potentially low costs.

Small quantities of levan are generally produced by sucrose fermentation using *Actinomyces viscosus* or *Aerobacter levanicum* strains.

*Bacillus polymixa* generally produces hetero-polysaccharides having different forms of polymers. Genetically modified *E. coli* strains have been used for producing levan (Gay, P. et al., 1983. J. Bacteriol. Vol. 153, p. 1424). Furthermore, other aerobic fermentation methods have also been used for producing levan (Jeanes, et al., U.S. Pat. No. 2,673,828; Gaffor, et al., U.S. Pat. No. 3,879,545; Ayerbe, et al., U.S. Pat. No. 4,399,221). The drawback of such processes is that they produce low product yield and problems related to contamination, thereby industrial processes leading to greater productivity are required.

DESCRIPTION OF THE INVENTION

The main purpose of this invention is to provide a biopolymer, produced by an enzymatic extract or preparation having glucosyltransferase and fructosyltransferase activity. It is produced from a *Lactococcus lactis* strain (NRRL B-30656) characterised by its high transfer activity, allowing the biopolymer to be obtained by a simple production method which is easy to scale-up. The biopolymer, obtained from *Lactococcus lactis* strain (NRRL B-30656), metabolism products maintains a 0.2 to 0.7 glucose/fructose ratio. The biopolymer is characterized by presenting the following properties: 900-11,000 Kilodalton molecular weight; two glass transition points; the first between 20° C. and 30° C. and the second between 190° C. and 220° C.; stability in aqueous solutions, pH values ranging from 2 to 9; 1,000 to 3,000 centipoises viscosity when the polymer was at 10% to 20% concentration in an aqueous solution at 30° C.; non-hygroscopic; and highly soluble in water, able to form hydrogel homogeneous dispersions at maximum 50% weight/volume concentration. Its production comprises the following steps: Phase 1: fermentation with the *Lactococcus lactis* NRRL B-30656 strain in a culture medium developed for this microorganism's growth; Phase 2: extracellular enzyme recovery trough centrifuging or ultra-filtration; Phase 3: biopolymer production trough enzyme reaction using sucrose as substrate and the enzymatic extract or preparation; and Phase 4: biopolymer purification through precipitation with solvents or ultra-filtration followed by drying the product.

DETAILED DESCRIPTION OF THE INVENTION

The object of the invention is to produce a polysaccharide contaminants-free pure biopolymer. The biopolymer can be described as being a polymer produced by a *Lactococcus lactis* strain isolated from soil. This strain has high transfer activity, leading to obtaining the biopolymer through a simple process, having a purity greater than 95%.

The Microorganism.

The *Lactococcus lactis* NRRL B-30656 strain is isolated from soil in the present invention by a selective process using a sucrose-containing medium as a carbon source in which the microorganisms producing the enzymatic extract or preparation having glucosyltransferase and fructosyltransferase activity, are able to use the substrate and to produce the polymers, giving the colony a mucoid aspect. Microorganisms having these characteristics are selected from this medium and purified trough isolating techniques involving successive dilutions and plate isolation. The *Lactococcus lactis* NRRL B-30656 strain was obtained from these strains and was used in the present invention.

In accordance with the present invention, the *Lactococcus lactis* NRRL B-30656 strain has been deposited in the Agricultural Research Service Patent Culture Collection NRRL Reference Bank at 1815 N. University Street, Peoria Ill. 61604 U.S.A. on May 15, 2003 under the Budapest Treaty on the International Recognition of the Deposit of Microorganisms for the purpose of Patent Procedure (e.g. see 961 OG 21, 1977); it was assigned registration number NRRL B-30656 by this institution. This strain produces an enzyme having 2-6 U/ml glucose transfer activity, using sucrose as substrate and also produced a 900-1,100 K Dalton molecular weight glucose and fructose polymer.

The strain is called NRRL B-30656. This strain was isolated and characterised at the Universidad Nacional de Colombia's Instituto de Biotecnologia (IBUN). The strain is kept at 4° C. in Petri dishes with a culture medium whose composition is: 10-40 g/l sucrose, 7-30 g/l yeast extract, 5-20 g/10.05-05 g/l potassium phosphate, 10-100 ppm mineral salts, pH 5-9.

The microorganism was characterised by optical microscopy using Gram staining and electronic transmission microscopy by means of positive staining with uranyl acetate and lead citrate. The biochemical characterisation was done using the computerised MicroScan system, according to that described in Bergey's determinative bacteriology manual (Stanley, W; Sharpe, E; Holt, J. 1994. Bergey's Manual of Systematic Bacteriology, William and Wilkins, Baltimore).

Culture Medium.

A balance was carried out between carbon source, nitrogen source and certain trace elements for designing and optimising the culture medium for the fermentation with the NRRL B-30656 *Lactococcus lactis* strain. The culture medium provides the microorganism with the nutrients needed for growing and producing the enzyme.

The following concentrations were established, as a result of evaluating culture medium components:

| Component | Concentration (g/l) |
|---|---|
| Salts | |
| $K_2HPO_4$ | 7–30 |
| $FeSO_4 \cdot 7H_2O$ | 0.01–1 |
| $MgSO_4 \cdot 7H_2O$ | 0.01–0.1 |
| $MnSO_4 \cdot H_2O$ | 0.001–0.1 |
| $CaCl_2 \cdot 2H_2O$ | 0.001–0.01 |
| NaCl | 0.01–0.1 |
| Carbon source | |
| Sucrose | 10–40 |
| Nitrogen source | |
| Yeast extract | 7–30 |

The pH is set to pH 5-9 with HCl. The medium is sterilised at 121° C. for 15 minutes.

Fermentation.

The pre-inoculums corresponding to 5-20% of the inoculum volume are activated from the pure strain preserve at −70° C. in a medium having 20% glycerol; incubation time should not exceed 10-36 hours during which time pre-inoculum purity must be verified. These cultures are done in flasks with stirring, occupying 5-20% total volume; they are incubated at 20-40° C. with 100-400 rpm stirring rate in orbital agitators. The number of inoculums necessary is determined by the number and size of the fermenters.

Growth and enzyme production conditions are 20-40° C. temperature with stirring at a rate of 100-400 rpm (depending on the fermentation scale).

Aeration.

The fermentation promoting microorganism is aerobic, meaning that the culture had to be aerated with 0.1-1 volumes of air per medium volume per minute (vvm) and pH is kept between 5 and 9 during fermentation. Culture mediums resulting from this production process have combinations of components in order to obtain final biomass concentration of 10-30 g/l, a wet weight, having 2-6 U/ml transfer activity, this being achieved in 6-24 hours.

Enzyme Recovery.

Extra-cellular enzyme are collected from fermented culture medium through centrifuging at 3,000-10,000 rpm for 15 minutes or by separating the biomass through filtration. Enzymatic extract or preparation thus presents 2-6 U/ml glucosyltransferase and fructosyltransferase activity.

Biopolymer Production

Enzymatic Reaction.

Reaction conditions are as follows:

| Reaction medium: | |
|---|---|
| 50-300 Mm phosphate buffer pH: | 5-9 |
| Substrate: | 5-40% sucrose |
| Quantity of enzyme: | 10-40% v/v enzymatic extract or preparation |
| Reaction time: | 12-48 hours |
| Stirring: | 100-400 rpm |

Biopolymer Recovery and Purification

After the enzymatic reaction, the temperature is reduced to 4° C. following enzymatic reaction and the biopolymer was recovered in two ways:

a) Precipitation with Solvents

96% ethanol is added to the cold reaction mixture with stirring. The added amount of ethanol corresponds to 1.2-2.0 volumes of ethanol/reaction mixture volume.

The precipitated biopolymer is redissolved in half the volume of deionised and distilled water and precipitated again with 1.2-2.0 volumes of ethanol/reaction mixture volume.

The precipitated biopolymer is redissolved in a third the volume of water and dried by lyophilisation or dried by compressed air at 60° C. until reaching 5-6% Humidity.

b) Ultrafiltration

The reaction mixture is submitted to ultra-filtration through a regenerated cellulose membrane having a pore size greater than 10,000 Dalton to eliminate residual glucose and fructose. The biopolymer is then submitted to aspersion drying.

The biopolymer is characterised by high performance liquid chromatography and 10% solution viscosity at 30° C. The biopolymer presents a 7-7.5 minutes retention time using a Shodex SC 1011 column at 70° C., 0.6 ml/min flow and HPLC grade water as mobile phase.

The viscosity of a 10% solution at 30° C. was found to range from 1000-3000 centipoises (cP) using a ViscoEasy viscosimeter (Serie L, Schott, Ref. 28.541.120) L2 stem at 50 rpm.

Average DVS (diameter/volume/surface) particle size is 224 micron. The biopolymer has a true density close to that of sucrose (1.5 mg/ml). It is a material presenting high interparticle porosity (48%).

EXAMPLES

The following examples are given to illustrate the present invention.

Example 1

Isolating and Identifying the Biopolymer-Producing Microorganism

A biopolymer-producing bacterium was isolated from soil and identified as being *Lactococcus lactis* NRRL B-30656. 10 g samples were collected from soil and grown in 100 ml liquid medium containing sucrose as carbon source. This was incubated at 30° C. with stirring for 24 hours. 4×1:10 dilutions were done in saline solution once growth was obtained; the fourth dilution was seeded. This culture was re-seeded in solid medium using the same composition and isolations were done, selecting the colonies showing polymer production. The culture was then transferred to a fresh medium and cultured for 24 hours. The microorganism was kept in a sucrose medium with 20% glycerol at −70° C. and by lyophilisation using 10% skimmed-milk, once it had been isolated.

The isolated strain, cultivated in solid sucrose medium, showed the following macroscopic characteristics: clear, cream-coloured, rubbery, circular colonies having a defined edge of around 2 to 3 mm diameter (in 24 hours culture). Gram cocci were observed by microscope via Gram staining; they were occasionally found individually but were generally seen forming groups.

Electronic transmission microscopy characterisation led to observing circular cells in which the cell wall could be differentiated. No special structures were observed (i.e. electro-dense granules, flagella, fimbria, etc).

The strain of the present invention is *Lactococcus lactis* NRRL B-30656, catalogued as GRASS microorganism and shows the following biochemical characteristics:

| Test | Result |
|---|---|
| Growth at 10° C. | Positive |
| Growth at 15° C. | Positive |
| Growth at 42° C. | Negative |
| Growth at pH 4.8 | Positive |
| Growth at pH 6.5 | Positive |
| Growth at pH 9.2 | Doubtful |
| Growth in 0.5% NaCl | Positive |
| Growth in 4% NaCl | Positive |
| Growth in 5% NaCl | Positive |
| Growth NaCl 6.5% | Positive |
| Growth in 10% NaCl | Negative |
| Growth in 15% NaCl | Negative |
| Catalase | Negative |
| Haemolysis | Gamma |
| Motility | Negative |
| Vogees-Proskauer | Positive |
| Aerobic glucose | Positive |
| Anaerobic glucose | Positive |
| Gas production | Negative |
| Aerobic lactose | Positive |
| Anaerobic lactose | Positive |
| Gas production | Negative |
| Aerobic fructose | Positive |
| Anaerobic fructose | Positive |
| Gas production | Negative |
| Aerobic maltose | Positive |
| Anaerobic maltose | Positive |
| Gas production | Negative |
| Aerobic manitol | Doubtful |
| Anaerobic manitol | Doubtful |
| Gas production | Negative |
| Aerobic galactose | Positive |
| Anaerobic galactose | Positive |
| Gas production | Negative |
| Aerobic sucrose | Positive |
| Anaerobic sucrose | Positive |
| Gas production | Negative |
| Aerobic xylose | Doubtful |
| Anaerobic xylose | Doubtful |
| Gas production | Negative |
| Aerobic rafinose | Positive |
| Anaerobic rafinose | Positive |
| Gas production | Negative |
| Ribose | Positive |
| Trealose | Positive |
| Sorbitol | Positive |
| Mannose | Positive |
| Arabinose | Positive |
| Arginin | Positive |

Example 2

Extract Production or Enzymatic Preparation

1. Fermentation:
a) Microorganism Activation

The *Lactococcus lactis* NRRL B-30656 microorganism was used for obtaining an enzymatic extract or preparation having glucosyltransferase and fructosyltransferase activity. Bacteria were stored in a cryoprotection solution (glycerol) at −70° C. The strain was slowly unfrozen until room temperature was reached and it was activated in 50 ml sucrose medium at 30° C. for 12 hours and stirring at 180 rpm. 5 ml of this culture were used for two types of seeding. The first in agar sucrose, incubated at 30° C. for 24 hours, while observing its mucoid characteristics and then stored at 4° C.; the second in 100 ml sucrose broth incubated at 30° C. for 12 hours. The latter was distributed in 1 ml centrifuge tubes with 20% v/v glycerol and stored at −70° C., for later use in fermentations. The remaining 45 ml of initial culture were preserved in 5 ml vials, lyophilised using 10% concentration sterile skimmed milk as support and stored at 4° C.

b) Preparing Pre-Inoculums and Inoculums

Pre-inoculums were prepared with the same medium composition corresponding to the batch; the microorganism conserved in solid sucrose medium was taken, then seeded in a volume of liquid medium, at 5-20% inoculum volume, cultured at 25-35° C., with stirring at 100-400 rpm for 12-24 hours.

Composition of the Medium Used:

| Component | concentration (g/l) |
|---|---|
| Salts: | |
| $K_2HPO_4$ | 10–20 |
| $FeSO_4 \cdot 7H_2O$ | 0.03 |
| $MgSO_4 \cdot 7H_2O$ | 0.02 |
| $MnSO_4 \cdot H_2O$ | 0.002–0.1 |
| $CaCl_2 \cdot 2H_2O$ | 0.0015–0.015 |
| NaCl | 0.01–0.1 |
| Carbon source: | |
| Sucrose | 15–30 |
| Nitrogen source: | |
| Yeast extract | 15–30 |

The microorganism was seeded at 5-10% of the fermentation volume and grown up to an average optical density of around 0.7 absorbance units in 1:10 dilution, read at 600 nm. A sterile culture medium was used as target.

A preinoculum and inoculum must be made during fermentation, depending on fermenter volume, in such a way that the necessary quantity of cells is obtained in final inoculum (10% culture medium deposited in the production fermenter) to avoid the latency phase in the reactor and trying to maintain the 1:10 volume ratio between the preinoculum and the inoculum or sufficient cell density to serve as inoculum, maintaining rigorous control over culture purity and vegetative state so that it can be used as either inoculum or preinoculum.

c) Preparing the Culture Medium and Inoculation

Culture medium pH was adjusted to pH 7.0. The balloon flask containing the medium for preparing the preinoculum was sterilised at 121° C. for 15 minutes.

d) Operating Conditions

Active ingredient was produced by batch fermentation using the established medium. The operating conditions are listed in the following Table.

Fermenter Operating Conditions

| Conditions | 141 |
|---|---|
| Medium volume (l) | 10 |
| Medium volume/fermenter volume ratio | 0.8 |
| Inoculum percentage | 5–10 |
| Inoculation optical density | 0.5–1 |
| Stirring (rpm) | 100–400 |
| Temperature (° C.) | 25–35 |
| Aeration (vvm) | 1–3 |
| Initial medium pH | 5–8 |
| Fermentation time (hours) | 6–12 |

2. Enzyme Recovery:
a) Centrifuging

Extracellular enzyme was recovered by centrifuging at 5,000 rpm for 15 minutes for separating the biomass. The enzymatic extract or preparation presented 2-6 U/ml glucosyltransferase and fructosyltransferase activity.

b) Ultrafiltration

Another way of recovering fermentation supernatant is by using 0.22-2 micron pore size ultra filtration membranes.

Example 3

Biopolymer Production and Recovery a) Enzymatic Reaction.
Reaction conditions were as follows:

| Reactant medium: | |
|---|---|
| 50-200 Mm phosphate buffer pH: | 5-7 |
| Substrate: | 8-20% sucrose |
| Enzyme quantity: | 10-30% v/v enzyme extract (200-500 U/l). |
| Reaction time: | 20-40 hours |
| Stirring: | 100-400 rpm |

The enzyme was separated by centrifuging, placed in medium containing 8-20% sucrose, at pH 5-8 and 25-35° C. for 20-30 hours, obtaining 30-60 g/l polymer concentration corresponding to 40-60% yield regarding substrate. Other processes reported to date have required up to 5-10 days for producing polymer. The reported microorganisms produced less polymer concentration (See Table 1).

b) Purifying the Biopolymer

After the enzymatic reaction, the temperature was lowered to 4° C. following enzyme reaction and it was possible to recover the biopolymer in two ways:

Precipitation with Solvents.
96% ethanol was added to cold reaction mixture with stirring. The quantity of added ethanol corresponded to 1.2-2.0 volumes of ethanol/volume reaction mixture.
The precipitated biopolymer was dissolved in half the volume of deionised and distilled water and precipitated again with 1.2 to 2.0 volumes of ethanol/reaction mixture volume.
Precipitated biopolymer was redissolved in a third of the volume of water and dried by lyophilisation or dried by compressed air at 60-80° C. until reaching 5-10% humidity.

TABLE 1

EPS production using different microorganisms

| Organism | Biopolymer (g/100 ml) |
|---|---|
| *Acetobacter pasteurianus* | |
| ATCC 11142 | 0 |
| *B. polymyxa* | |
| NRRL B-68 | 0 |
| NRRL B-130 | 0 |
| NRRL B-510 | 1.2 |
| NRRL B-4317 | 1.4 |
| Isolate (NRRL B-18475) | 3.6 |
| *B. subtilis* | |
| NRRL B-447 | 1.0 |
| NRRL B-577 | 0 |
| NRRL B-644 | 0 |
| NRRL B-675 | 1.0 |
| NRRL B-744a | 1.5 |
| NRRL B-2612 | 0 |
| *Enterobacter levanicum* | |
| NRRL B-1678 | 0.7 |
| *Microbacterium laevaniformans* | |
| ATCC 15953 | 1.2 |

Ultrafiltration.

The reaction mixture was submitted to ultrafiltration on a regenerated cellulose membrane having a pore size greater than 10,000 Daltons to eliminate residual glucose and fructose. The biopolymer was then dried by aspersion process.

Biopolymer production by this microorganism depends on the substrate concentration, this being optimal at 8-24% where the biopolymer is produced having the greatest degree of purity with the greatest yield (Table 2).

TABLE 2

Effect of sucrose on biopolymer production by *Lactococcus lactis*

| | Sucrose (%) | Biopolymer (g/l) |
|---|---|---|
| Control | 0 | 0% (sucrose free) |
| Sucrose | 8 | 38.8 |
| Sucrose | 12 | 50.1 |
| Sucrose | 16 | 55.6 | c) Drying

The final product was obtained as a white powder which could be dried by lyophilisation or dry heat at a temperature not greater than 80° C.

Example 4

Biopolymer Characterisation

1. Solubility

The product was a hydro-soluble biopolymer able to form hydrogel homogeneous dispersions up to 50% maximum concentration. 1.0 g of biopolymer was dissolved in 32 ml 5% chlorhydric acid, in 50 ml 10% sodium hydroxide and in 30 ml glacial acetic acid.

It was insoluble in ethanol, isopropanol, acetone, mineral and vegetal oil and polyethylen glycol.

The product was moderate soluble in 0.5% oxalic acid at ebullition temperature.

2. High Performance Liquid Chromatography (HPLC).

A 1.5% biopolymer solution presented a 900-1,100 KDa molecular weight in permeation chromatography determined on a Shodex OHPak KB-803 column. Chromatography conditions were as follows:

| | |
|---|---|
| Temperature: | 55° C. |
| Mobile phase: | 0.1 M NaCl solution |
| Flow: | 0.9 ml/min |

Polymer purity was greater than 95%, revealed by a thin peak in HPLC, in the following conditions:

| | |
|---|---|
| Column: | Shodex SC1011 |
| Mobile phase: | distilled deionised water |
| Flow: | 0.6 ml/min. |
| Temperature: | 70° C. |
| Equipment: | Waters 510 with refraction index detector (Waters 2410). |

The biopolymer presented a 7 to 7.5 minute retention time under these conditions.

The patterns used were analytic reagent grade glucose, fructose, and sucrose.

The biopolymer was stable over a broad range of pH shown by HPLC after contacting the polymer with pH 2-9 buffers.

3. Viscosity

Viscosity was determined in a 10% solution at 30° C. using a ViscoEasy viscosimeter Serie L, Schott, Ref. 28.541.120, L2 stem at 50 rpm. The samples analysed presented viscosity ranging from 1,000-3,000 centipoises (cP). Pseudo-plastic behaviour was exhibited (cross-sectional thinning). Biopolymer solution viscosity became reduced on increasing the shear rate and increased on reducing temperature.

4. Dimensional Characteristics

The biopolymer had a true density close to that of sucrose (1.5 mg/ml). It is a material presenting high inter-particle porosity (48%).

Average DVS particle size (diameter/volume/surface) was 224 micron.

5. Humidity Adsorption

Water adsorption capacity ranged from 6.12 mg/g to 353.20 mg/g depending on relative humidity; this means that it was a slightly hygroscopic material. The biopolymer was capable of unlimited expansion on contact with water due to its polymeric structure and hydrophilicity, being able to form variable consistency systems depending on the quantity of water incorporated, giving rise to forming aqueous dispersions characterised by their high viscosity.

6. Humidity

It presents losses of up to 10% when dried in a vacuum oven at 60° C.

7. Thermal Characteristics

The biopolymer presents two vitreous transition points; the first between 20° C. and 30° C. and the second between 190° C. and 220° C. as determined by differential scanning calorimetry.

8. Microbiological Quality

The biopolymer presents the following microbiological counts:

| Microbiological charge | Range | Unit |
|---|---|---|
| Viable mesophile count | 2000–4000 | ufc/gr |
| *Coliform* count | Absence | nmp/gr |
| *Faecal coliform* count | <10 | nmp/gr |
| *Salmonella* count | Absence | |
| mildew and yeast count | 2000–5000 | ufc/gr |

9. Uses a) The biopolymer could be used in the pharmaceutical industry as viscosant, thickener, stabiliser, dispersant, as a film former, as disintegrant, blood plasma substitute, lubrication agent and/or prebiotic agent.

b) The biopolymer could be used in the food industry as a thickener, viscosant, stabiliser, dispersant, as fibre and as fat, oils and ether- and ester-based carbohydrates substitute.

c) The biopolymer can be used in products obtained by extrusion, for forming films apt for producing flexible and biodegradable packages and for obtaining disposable biodegradable products, obtained by injection or moulding and in the production of flocculent agents for water treatment.

We claim:

1. An isolated and purified glucose and fructose biopolymer having a 0.2 to 0.7 glucose/fructose ratio,
   wherein the biopolymer has the following properties:
      900-1,100 Kilodalton molecular weight;
      two vitreous transition points, the first between 20° C. and 30° C. and the second between 190° C. and 220° C.;
      stability in aqueous solutions, pH values ranging from 2 to 9;
      1,000 to 3,000 centipoise viscosity when the polymer is at 10% to 20% concentration in an aqueous solution at 30° C.;
      water adsorption capacity of 6.12 mg/g to 353.20 mg/g depending on relative humidity; and
      highly soluble in water, able to form hydrogel homogeneous dispersions at maximum concentration of 50% w/v,
   and wherein the biopolymer is prepared by:
      a) fermenting *Lactococcus lactis* strain (NRRL B-30656) in a culture medium developed for this microorganism's growth,
      b) recovering an extracellular enzyme extract excreted from the *Lactococcus lactis* strain (NRRL B-30656) into the culture medium by centrifuging or ultra-filtration,
      c) incubating the extracellular enzyme extract from the *Lactococcus lactis* strain (NRRL B-30656) with a sucrose substrate, wherein the extracellular enzyme extract comprises glucosyltransferase and fructosyltransferase activity, thereby obtaining the biopolymer via an enzymatic reaction, and
      d) recovering and purifying the biopolymer, and wherein hexoses in the isolated and purified biopolymer consist only of fructose and glucose.

2. A method for producing an isolated and purified glucose and fructose biopolymer, comprising:
   a) fermenting *Lactococcus lactis* strain (NRRL B-30656) in a culture medium,
   b) recovering an extracellular enzyme extract excreted from the *Lactococcus lactis* strain (NRRL B-30656) into the culture medium by centrifuging or ultrafiltration,
   c) incubating a medium comprising the extracellular enzyme extract from the *Lactococcus lactis* strain (NRRL B-30656) and a sucrose substrate, wherein the extracellular enzyme extract comprises glucosyltransferase and fructosyltransferase activity, thereby obtaining the biopolymer via an enzymatic reaction, and d) recovering and purifying the biopolymer by precipitation or ultrafiltration wherein the biopolymer has the following properties:

900-1,100 Kilodalton molecular weight;

two vitreous transition points, the first between 20° C. and 30° C. and the second between 190° C. and 220° C.;

stability in aqueous solutions, pH values ranging from 2 to 9;

1,000 to 3,000 centipoise viscosity when the polymer is at 10% to 20% concentration in an aqueous solution at 30° C.;

water adsorption capacity of 6.12 mg/g to 353.20 mg/g depending on relative humidity; and highly soluble in water, able to form hydrogel homogeneous dispersions at maximum concentration of 50% w/v.

3. The method for producing the biopolymer, according to claim 2, wherein the incubation step further comprises:

stirring the medium comprising the extracellular enzyme extract and the sucrose substrate at a speed ranging from 100-400 revolutions per minute, wherein the pH of the medium ranges from 5 to 9, the amount of extracellular enzyme extract in the medium ranges from 10-40% v/v, and the sucrose substrate concentration ranges from 5-40%; and incubating the medium at a reaction time ranging from 12-48 hours, at a temperature ranging from 25°-35° C.

4. The method according to claim 2, wherein the step of recovering and purifying the biopolymer through precipitation comprises:

a) adding 1.2-2.0 volumes of 96% ethanol to a cold reaction mixture with stirring, wherein the quantity of added ethanol corresponds to an ethanol/reaction mixture volume, thereby obtaining a precipitated biopolymer;

b) redissolving the precipitated biopolymer obtained in step a) in half the volume of deionized and distilled water and precipitating the biopolymer obtained in step a) again with 1.2 to 2.0 volumes of an ethanol/reaction mixture volume; and c) redissolving the precipitated biopolymer in a third of the volume of water and drying through lyophilization or compressed air drying between around 50° C. to 80° C. until reaching around 5-6% humidity.

5. The method according to claim 2, wherein the step of recovering and purifying the biopolymer through ultrafiltration comprises:

ultrafiltrating a reaction mixture comprising the biopolymer with a regenerated cellulose membrane having a pore size between 10,000-30,000 Dalton for separation by size exclusion to eliminate residual glucose and fructose and submitting the biopolymer to aspersion drying.

6. A composition comprising the fructose and glucose biopolymer according to claim 1, wherein the composition is a viscous agent, thickener, stabilizer, dispersant, film forming agent disintegrating agent, blood plasma substitute, lubricating agent or prebiotics agent.

7. A flexible and biodegradable film comprising the biopolymer according to claim 1.

* * * * *